United States Patent
Conrad et al.

(10) Patent No.: US 6,280,633 B1
(45) Date of Patent: Aug. 28, 2001

(54) OZONE SENSOR AND METHOD FOR USE OF SAME IN WATER PURIFICATION SYSTEM

(75) Inventors: Wayne Ernest Conrad, Hampton; Richard M. Duff, Oshawa; Terry B. Bohrsen, Orono, all of (CA)

(73) Assignee: Fantom Technologies Inc., Welland (CA)

( * ) Notice: Subject to any disclaimer, the term of this patent is extended or adjusted under 35 U.S.C. 154(b) by 0 days.

(21) Appl. No.: 09/452,429

(22) Filed: Dec. 1, 1999

(51) Int. Cl.⁷ ............................. B01D 17/12; G01N 27/00
(52) U.S. Cl. ................. 210/739; 210/96.1; 210/192; 210/188; 210/746; 210/760; 422/98; 422/186.01; 436/155; 340/632
(58) Field of Search ................ 210/85, 96.1, 138, 210/139, 143, 192, 739, 746, 760, 188; 422/29, 30, 98, 186.07, 186.14; 436/55, 135; 340/632, 633, 660, 661

(56) References Cited

U.S. PATENT DOCUMENTS

| | | | |
|---|---|---|---|
| 4,368,431 | 1/1983 | Rohr et al. | 324/624 |
| 4,409,183 | * 10/1983 | Fisher | 436/135 |
| 4,599,166 | 7/1986 | Gesslauer | 210/96.1 |
| 4,885,929 | 12/1989 | Kasahara et al. | 422/98 |
| 5,053,140 | * 10/1991 | Hurst | 210/760 |
| 5,071,626 | 12/1991 | Tuller | 422/98 |
| 5,167,927 | 12/1992 | Karlson | 422/90 |
| 5,172,066 | 12/1992 | Succi et al. | 324/693 |
| 5,270,009 | 12/1993 | Nakamori et al. | 422/98 |
| 5,364,537 | 11/1994 | Paillard | 210/743 |
| 5,389,340 | 2/1995 | Satake | 422/98 |
| 5,427,693 | 6/1995 | Mausgrover et al. | 210/748 |
| 5,498,347 | 3/1996 | Richard | 210/760 |
| 5,683,576 | 11/1997 | Olsen | 210/138 |
| 5,695,635 | 12/1997 | Sasaki et al. | 210/188 |
| 5,785,864 | 7/1998 | Teran et al. | 210/739 |
| 6,039,884 | * 3/2000 | Burris et al. | 210/760 |

FOREIGN PATENT DOCUMENTS

| | | |
|---|---|---|
| 1297948 | 3/1992 | (CA). |
| 2193645 | 12/1995 | (CA). |
| 2225483 | 11/1996 | (CA). |
| 2235256 | 4/1997 | (CA). |
| 2081572 | 12/1997 | (CA). |
| 2236765 | 11/1998 | (CA). |

OTHER PUBLICATIONS

Carus Chemical Company Product Disclosure—Carulite® 200 Catalyst (5 pages), Undated.

* cited by examiner

Primary Examiner—Joseph W. Drodge
(74) Attorney, Agent, or Firm—Bereskin & Parr

(57) ABSTRACT

A liquid purification apparatus which uses ozone to purify water is disclosed. Off-gas from the purification process is passed through an ozone detector that provides an electric signal corresponding to the ozone concentration in the off-gas. The electric signal is monitored and used to control the length of the ozonation process. The detector comprises a $MgO_2$ and $CuO$ based ozone destroying catalyst which generates an electric potential when used to decompose ozone into oxygen.

31 Claims, 3 Drawing Sheets

OZONE SENSOR AND METHOD FOR USE OF SAME IN WATER PURIFICATION SYSTEM

FIELD OF THE INVENTION

This invention relates to gas concentration sensors and more particularly to a sensor for measuring the concentration of a gas such as ozone in a gas stream. The invention also relates to water purification systems and more particularly to a method and apparatus for sensing the concentration of a reactable gas (such as ozone) in an off-gas during a water purification process.

BACKGROUND OF THE INVENTION

In many areas, a reactable gas is used as a processing agent to treat a liquid. Examples of this include water treatment to remove waste or to create potable water and chemical oxidation (i.e. bleaching) processes.

In such processes, it is important to ensure that treatment of the liquid with the reactable gas continues for a sufficient period that the desired treatment result is achieved. In water treatment applications, commonly used reactable gases include ozone and hydrogen peroxide. Ozone is used in many water treatment applications to remove impurities. It is important to ensure that ozonation of the water continues until the level of impurities has fallen to an acceptable level. One method of doing this is to fix the volume of water and then ozonate the water for a period that is known to be sufficient to reduce the impurity level, regardless of the initial concentration of impurities in the water. However, this method may waste ozone (if the initial level of impurities was relatively low) as well as requiring a fixed, and possibly lengthy, time for each ozonation process. It is preferable to use a system that monitors the impurity level and stops the ozonation process when the acceptable impurity level is achieved.

Accordingly, various different sensors have been developed to measure the level of ozone in water. Some of these sensors operate by passing ultraviolet light through a fluid stream and measuring the ultraviolet light received on a detector. Another type of gas detector is disclosed in U.S. Pat. No. 5,167,927 to Karlson. Karlson discloses a monitor which measures the heat energy released when a gas, e.g. ozone, is catalytically converted into a different compound, e.g. oxygen. A third type of sensor is disclosed in U.S. Pat. No. 5,427,693 to Mausgrover et al. Mausgrover incorporates a meter to measure the oxidation-reduction potential (ORP) of the water being cleaned. The ORP is then equated to an ozone concentration in the water. A fourth type of ozone sensor is disclosed in U.S. Pat. No. 5,683,576 to Olsen. In the system described by Olsen, an ozone containing gas is passed through contaminated water until the concentration of ozone in solution in the water reaches a pre-determined level. Ozonation then continues for a pre-determined period. The objective of this system is to ensure that a specified volume of water will be treated with a specified concentration of ozone for a specified period of time.

Although these systems may provide a reliable measure of the concentration of ozone in water, none of them provides an accurate measure of the degree to which impurities have been removed from the water. Continuing ozonation after the desired ozone concentration is reached for a pre-determined period ensures only that a minimum amount of ozone passes through the water over the entire treatment period. Olsen assumes that once the concentration of ozone reaches the predetermined level, it does not subsequently fall. Further, Olsen assumes that simply allowing a selected concentration of ozone to remain in the water for a selected time ensures that the water is suitable for use. However, this will not necessarily be true, especially in the case of highly contaminated water. For example, lake or well water will normally require more treatment than treated water from a municipal supply.

SUMMARY OF THE INVENTION

Accordingly, there is a need for a method and apparatus to accurately measure, on an ongoing basis, the degree to which impure water has been treated by ozonation. This may be done by measuring the amount of ozone that passes through water in a water purification chamber without being consumed. As the amount of unconsumed ozone exiting the chamber rises, the level of impurities is known to have fallen. When the amount of unconsumed ozone exiting the chamber becomes substantially constant, the water may be reliably considered to be substantially free of impurities that are susceptible to removal by the ozone.

In accordance with a first aspect of the present invention, there is provided a sensor for detecting the concentration of ozone in an incoming gas stream, said sensor comprising a sensing element positioned in the flow path of the incoming gas stream, said sensing element being electrically sensitive to the presence of ozone such that an electrical potential corresponding to said concentration is induced across said sensing element; and an electrical circuit coupled to said sensing element for allowing said electrical potential to be measured.

In accordance with a second aspect of the present invention, there is provided an apparatus for removing impurities from water, said apparatus comprising: a contact chamber for containing said water, said contact chamber having a head space for containing an off-gas and said contact chamber having an off-gas outlet for allowing said off-gas to exit said contact chamber in an off-gas stream; a closure for providing a substantially gas tight seal between the interior and exterior of said contact chamber; a reactable gas source for providing a reactable gas; a reactable gas control for controllably introducing said reactable gas into said contact chamber; a reactable gas sensor for providing a reactable gas concentration signal corresponding to the concentration of reactable gas in said off-gas stream at a signal node, said reactable gas sensor having an off-gas inlet and said off-gas inlet being in fluid communication with said off-gas outlet; and a controller, said controller being coupled to said signal node for receiving said reactable concentration signal and to said reactable gas control for controlling the introduction of said reactable gas into said contact chamber in response to said reactable gas concentration signal.

In accordance with a third aspect of the present invention, there is provided a method of removing impurities from an impure liquid, said method comprising the steps of: providing a quantity of said impure liquid in a contact chamber; providing a controller for controlling the flow of a treatment gas containing a reactable gas into said chamber; initiating the flow of said treatment gas into said contact chamber, wherein said reactable gas flows through said liquid and wherein at least some of said reactable gas reacts with impurities in said liquid consuming at least some of said reactable gas, the remainder of said treatment gas collecting in said chamber as an off-gas; withdrawing some of said off-gas; monitoring the concentration of said reactable gas in said off-gas; and terminating the flow of said treatment gas in response to the rate of change of said concentration of said reactable gas in said off-gas falling below a selected level.

In accordance with a fourth aspect of the invention, there is provided a method of removing impurities from an impure liquid, said method comprising the steps of: providing a quantity of said impure liquid in a contact chamber; providing a supply of a reactable gas; providing a controller for controlling the flow of said reactable gas into said contact chamber; providing a sensor for measuring the concentration of said reactable gas in an off-gas stream exiting said chamber and providing an electrical signal corresponding to said concentration; initiating the flow of said reactable gas into said chamber wherein said reactable gas flows through said liquid, and wherein at least some of said reactable gas reacts with impurities in said liquid consuming at least some of said reactable gas, the remainder of said reactable gas exiting said chamber in said off-gas stream; monitoring said signal until the rate of change of said signal falls to a selected level; terminating the flow of said reactable gas.

BRIEF DESCRIPTION OF THE DRAWINGS

The present invention will now be explained by way of example only with reference to the drawings, in which.

DETAILED DESCRIPTION OF THE INVENTION

Figure 1:
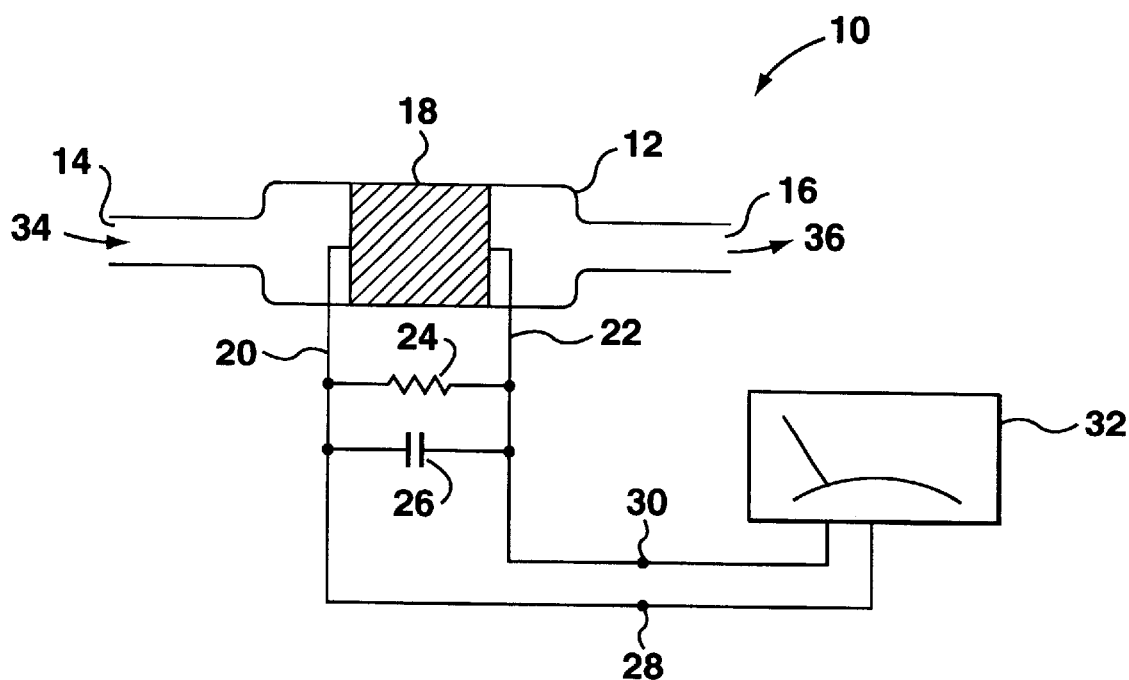
FIG. 1 is a perspective cut-away drawing of a preferred embodiment of an ozone sensor according to the present invention.

Reference is first made to FIG. 1, which shows a preferred embodiment of an ozone sensor 10 according to the present invention. Ozone sensor 10 comprises a housing 12 with a gas inlet 14 for receiving an incoming gas stream 34 and a gas outlet 16 for expelling an outgoing gas stream 36. Gas inlet 14 and gas outlet 16 are located at longitudinally opposed ends of housing 12. A sensing element 18 is positioned within housing 12.

Sensing element 18 is sensitive to the concentration of ozone in the incoming gas stream 34. An electrical potential is induced across sensing element 18 in the longitudinal direction (with respect to housing 12). Electrical lines 20 and 22 are coupled to the longitudinal ends of sensing element 18. Resistor 24 and capacitor 26 are coupled between lines 20 and 22 outside of housing 12.

Sensor 10 produces an electrical signal corresponding to the concentration of ozone in the incoming gas stream at terminals 28 and 30. A voltmeter 32 coupled to nodes 28 and 30 will show the magnitude of this electrical signal. The magnitude of the electrical signal may be correlated to the concentration of ozone in incoming gas stream 34 through simple experimentation, which will be within the ability of one skilled in the art. To simplify use of voltmeter 32 for this purpose, the scale of voltmeter 32 may be replaced with a scale indicating ozone concentration, thereby producing an ozone concentration meter.

In use, inlet 14 will be coupled to a gas source (not shown) and outlet 16 may be coupled to a gas processor (not shown). In the preferred embodiment, sensing element 18 is an ozone destroying substance comprising magnesium dioxide ($MgO_2$) and copper oxide (CuO). Such a material is commercially available from the Carus Chemical Company, 315 Fifth Street, Peru, Ill., USA 61354 (Telephone: 1-800-435-6856) under the trade name CARULITE® 200. CARULITE 200 is a catalyst that decomposes ozone into oxygen through a catalytic reaction. CARULITE 200 is not consumed in this reaction. In the preferred embodiment, sensing element 18 is a pellet of CARULITE 200. CARULITE 200 is porous and the catalytic reaction takes place as an air stream containing ozone passes through the pellet. Preferably, sensing element 18 is sized such that the outer surface of sensing element 18 is substantially in contact with the inner surface of housing 12 such that air stream 36 flows substantially through sensing element 18, rather around the outside of sensing element 18. The inventors have found that an electric potential is created across the CARULITE 200 pellet as ozone is decomposed into oxygen. Lines 20 and 22 carry this potential to terminals 28 and 30. Resistor 24 discharges the electrical potential across lines 20 and 22. Resistor 24 is chosen to have a high resistance (1–10 MΩ, and preferably 5–6 MΩ) so that the potential discharges slowly enough to permit voltmeter 30 to display the potential. Capacitor 26 acts as a filter to smooth the electric potential. Although resistor 24 and capacitor 26 are not essential to the operation of ozone sensor 10, their use is preferred to provide a smoother electrical signal which is responsive to changes in the ozone concentration in air stream 34 at terminals 28 and 30.

When CARULITE 200 is used as sensing element 18, the electrical signal produced by sensor 10 is a millivolt level signal. The inventors have found that this signal is essentially directly proportional to the concentration of ozone in the incoming gas stream.

In an alternate embodiment of ozone sensor 10, resistor 24 and capacitor 26 may be integrated within housing 12 and voltmeter 32 may be integrated onto the exterior of housing 12, providing a integral ozone sensor with a concentration meter. In another embodiment, terminals 28 and 30 may be left unconnected, providing an integral sensor which may be electrically coupled to a monitoring device, as is done in the water purification system described below with reference to FIG. 2.

Figure 2:
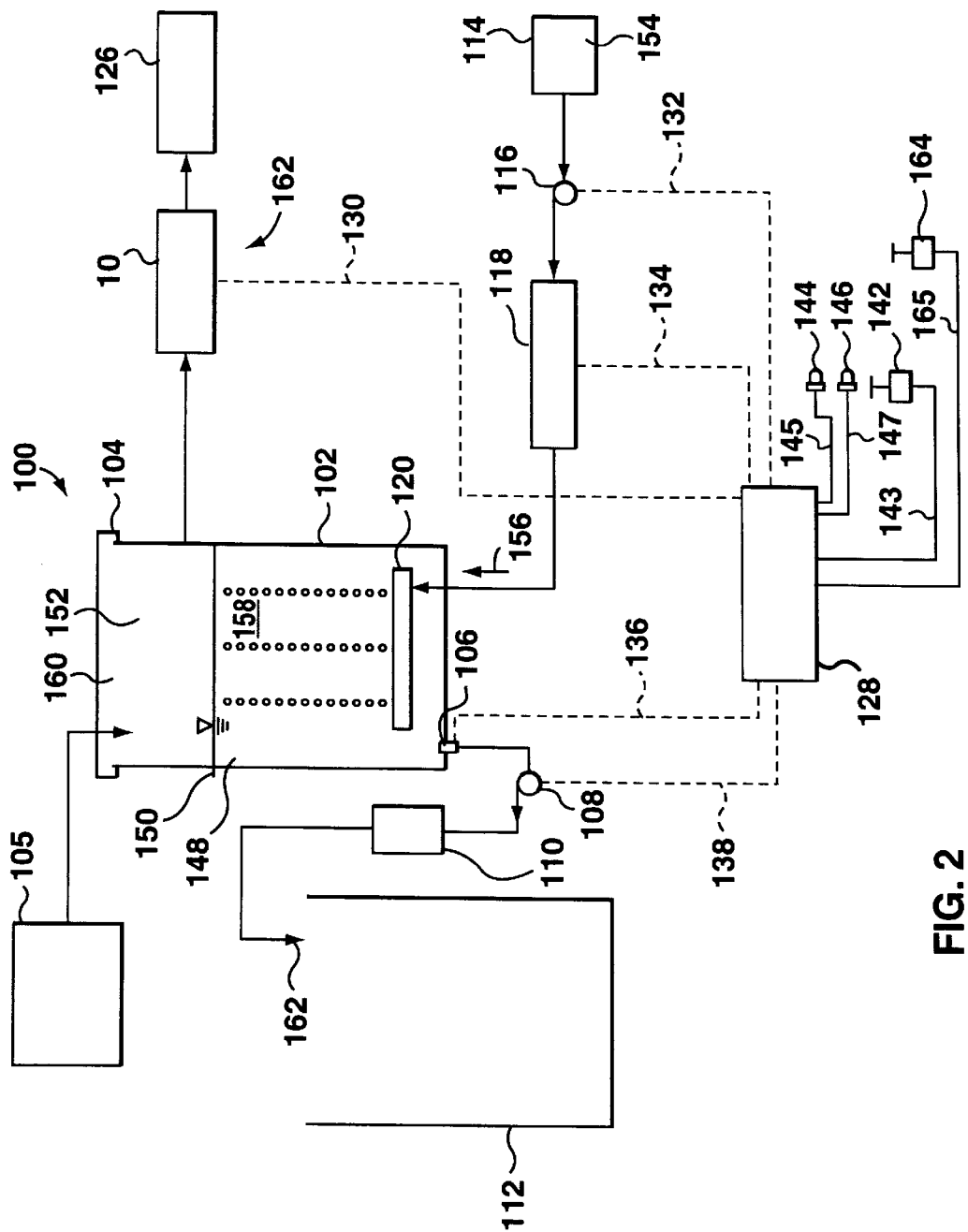
FIG. 2 is a schematic drawing of a preferred embodiment of a water purification apparatus incorporating the ozone sensor of FIG. 1.

Reference is next made to FIG. 2, which is a schematic diagram of a water purification system 100 for purifying contaminated water by bubbling ozone through the water.

Water purification system 100 comprises a contact chamber 102 with a sealing lid 104, water outlet valve 106, water pump 108 carbon filter 110 and clean water receptacle 112, oxygen source 114, oxygen pump 116, ozone generator 118, sparger 120, ozone sensor 10, ozone destroyer 126, controller 128 and a dispensing nozzle 162.

Ozone sensor 10 is identical to the ozone sensor of FIG. 1, except that it is not connected to voltmeter 32. Instead, nodes 30 and 38 of ozone sensor 10 are coupled to controller 128 by data line 130.

Controller 128 monitors and controls the water purification process. Controller 128 is connected to oxygen pump 116 by control line 132, to ozone generator 118 by control line 134, to water outlet valve 106 by control line 136 and to water pump 108 by control line 138.

Controller 128 is also coupled to a "Start Purification" button 142 by data line 143, to a "Clean" indicator light 144 by control line 145 and to a "Unable to Clean" indicator light 146 by control line 147. "Start Purification" button 142 may be a typical normally open pushbutton. Indicator lights 144 and 146 may be typical LEDs. In one embodiment, "Clean" indicator light 144 comprises a green LED and "Unable to Clean" indicator light 146 comprises a red LED. In another embodiment, both indicator lights 144, 146 are combined using a single combination red/green LED. Controller 128 is also coupled to a "Dispense Water" button 164 by control line 165.

Prior to initiating the purification process, the user of water purification system 100 pours water 148 into contact chamber 102 from impure water source 104 (which may be a municipal water supply). Water 148 contains impurities which may be neutralized by exposing them to ozone. The interior of contact chamber 102 is marked with a maximum water level 150 to indicate the maximum amount of water that may be put into contact chamber 102. Lid 104 fits onto contact chamber 102 to provide a gas-tight seal, providing a head space 152 between maximum water level mark 150 and lid 104. Gas inlet 14 of ozone sensor 10 is in fluid communication with head space 152.

Oxygen source 114 contains oxygen 154. Oxygen source 114 may be ambient air, air or another gas enriched with oxygen or pure oxygen.

To initiate the purification process, lid 104 is installed onto contact chamber 102 and the user presses "Start Purification" button 142. After "Start Purification" button 142 is pressed, controller 128 energizes oxygen pump 116 and ozone generator 118, which converts some of oxygen 154 into ozone 156. Ozone generator 118 will, in general, not convert all of the gas in oxygen source 114 into ozone 156 (even if oxygen source 114 is pure oxygen). The concentration of ozone in the output gas of ozone generator 118, defined here as $[O_3]_{gen-out}$, will depend on the concentration of oxygen 154 in oxygen source 114 and on the efficiency of ozone generator 118 in converting oxygen 154 into ozone 156. $[O_3]_{gen-out}$ may be calculated for a particular configuration of water purification system 100 (i.e. for a particular oxygen source 114 and a particular ozone generator 118).

Ozone 156, along with any gases not converted by ozone generator 118, is fed into sparger 120, which is located inside contact chamber 102. Sparger 120 disperses ozone 156 in finely separated bubbles 158 through water 148. Some of ozone 156 will react with impurities in water 148 to neutralize the impurities, consuming the ozone. Unreacted ozone 156, gaseous by-products of the reaction between ozone and the impurities and other gases not converted into ozone by ozone generator 118 will rise into head space 152 and collects as off-gas 160.

As off-gas 160 builds up in head space 152, some of off-gas 160 will be forced into ozone sensor 10. Off-gas 160 passes through ozone sensor 10 (where some of the ozone in off-gas 160 is decomposed into oxygen, as described above) to ozone destroyer 126, where the remainder of the ozone in off-gas 160 is destroyed. The resulting gas, which contains no or only a nominal amount of ozone is released into the ambient environment.

An electrical signal $V_{sensor}$ corresponding to the concentration of ozone in off-gas 160, defined here as $[O_3]_{off-gas}$, is transmitted by sensor 10 to controller 128 across data line 130 during the entire purification process. Controller 128 monitors $V_{Sensor}$ to control the purification process.

Figure 3:
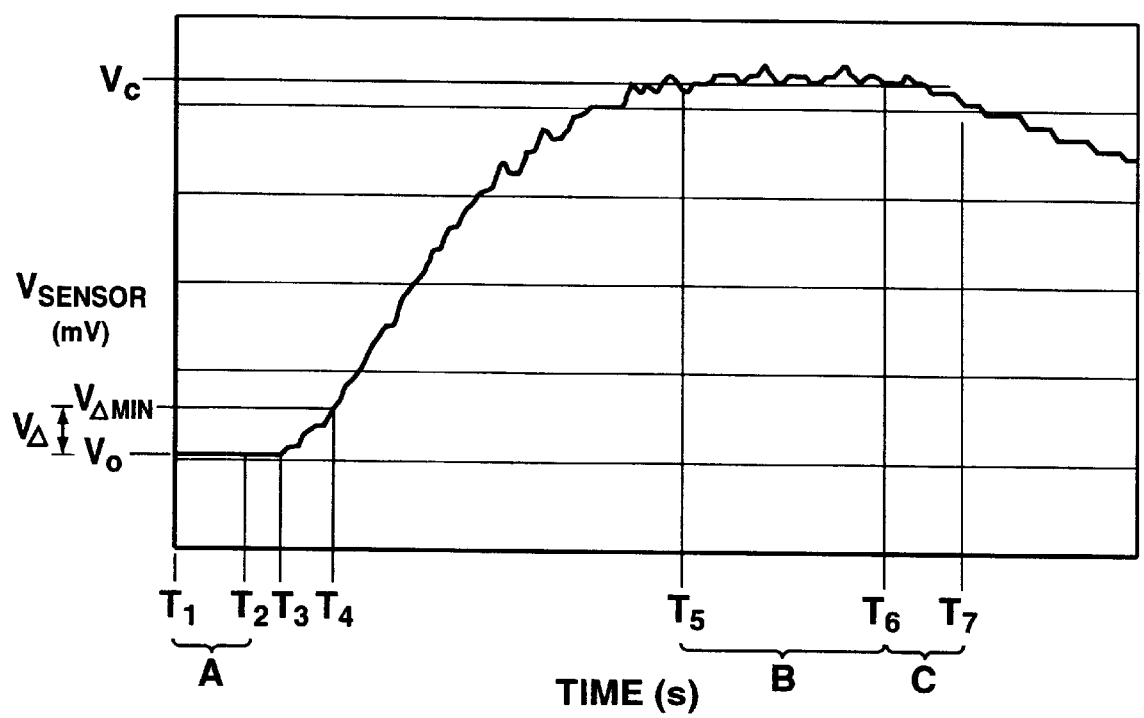
FIG. 3 is a graph of the output of the ozone sensor used in the water purification apparatus of FIG. 2 over time during a water purification cycle.

Reference is next made to FIG. 3, which is a graph of $V_{sensor}$ over time during a typical water purification cycle.

The purification process is started at time $T_1$ by the user pressing "Start Purification" button 142. Controller 142 records the value of $V_{sensor}$ at time $T_1$. This value is defined as $V_o$ and represents the condition where $[O_3]_{off-gas}$ is equal to zero (0). The inventors have found that $V_o$ varies for different samples of sensing element 18 and can vary for the same sensing element 18 at different times. Accordingly, measuring $V_o$ at the beginning of each purification cycle provides a self-calibration feature to ensure that the specific characteristics of the sensing element 18 do not affect the operation of water purification system 100. Although the cause of the variability of $V_o$ in different sensing elements 18 made of the same CARULITE 200 material is not fully understood, the inventors believe that this may relate to the sensitivity of the material to ambient temperature, variations in the manufacture of the material and possibly to residual electrical effects remaining from a previous operation of water purification system 100.

At time $T_2$, controller 128 energizes oxygen pump 116 and ozone generator 118. As shown in FIG. 3, time $T_2$ may be a selected period A after time $T_1$. Alternatively, time $T_2$ may occur immediately after $V_o$ has been recorded. Initially, ambient air that was sealed into head space 152 when lid 104 was placed onto contact chamber 102 will be forced through ozone sensor 10. Accordingly, $[O_3]_{off-gas}$ and $V_{sensor}$ will remain flat. At time $T_3$, the majority of this ambient air has passed through ozone sensor 10.

Starting at time $T_3$, some of ozone 156 will begin to pass through ozone sensor 10. Initially, a relatively large proportion of ozone 156 generated by ozone generator 118 will be consumed in removing impurities from water 148. As a result, $[O_3]_{off-gas}$ will be relatively low and $V_{sensor}$ will correspondingly be relatively low.

After time $T_3$, $[O_3]_{off-gas}$ will rise as the number of impurities remaining in water 148 falls. Generally, after some time, $V_{sensor}$ will exceed a selected voltage level $V_{min}$, which corresponds to a selected minimum increase in off-gas ozone concentration level $[O_3]_{off-gas(min)}$. This point is defined as time $T_4$. When $V_{sensor}$ exceeds $V_{min}$, it is assumed that the water purification process has been successfully commenced. $V_{min}$ is defined as a selected voltage $V_A$ greater than $V_o$. $V_A$ is selected to ensure that a non-nominal change in $[O_3]_{off-gas}$ must occur before it is assumed that the water purification process has been started properly. If $V_{sensor}$ does not exceed $V_{min}$, this may indicate that there is a problem with oxygen supply 114 (i.e. it does not contain oxygen 154), oxygen pump 116, ozone generator 118 or with the tubing connecting these elements to one another or to sparger 120. Controller 128 may record this information for use in maintaining or repairing water purification system 100.

After time $T_4$, controller 128 monitors $V_{sensor}$ until the rate of change of $V_{sensor}$ is approximately zero (i.e. the absolute value of the average of the derivative of $V_{sensor}$ over a selected period is less than a selected voltage). This is defined as time $T_5$ and the value of $V_{sensor}$ at time $T_5$ is defined as $V_C$. When $V_{sensor}$ levels off, as shown in FIG. 3 immediately prior to time $T_5$, this indicates that $[O_3]_{off-gas}$ has levelled off, indicating that almost no ozone is being consumed to remove impurities from water 148. Accordingly, it is assumed that most impurities in water 148 susceptible to removal by ozonation have been removed or neutralized. The inventors have found that at time $T_5$, $[O_3]_{off-gas}$ is approximately equal to $[O_3]_{gen-out}$.

Time $T_6$ is a selected time period B after time $T_5$. Period B is chosen to ensure that sufficient ozonation of water 148 is performed to remove almost all remaining impurities in water 148 that are susceptible to removal by ozonation are removed without unduly extending the length of the water purification process.

At time $T_6$, controller 128 de-energizes ozone generator 118. The operation of oxygen pump 116 is continued. The result is that gas from oxygen source 114 is bubbled directly through water 148, into head space 152 and into ozone sensor 10. Ozone dissolved in water 148 will be removed by the gas from oxygen source 114 and $[O_3]_{off\text{-}gas}$ will fall, as shown after time $T_6$.

Time $T_7$ is a selected time period C after time $T_6$. Period C is chosen to ensure that any ozone dissolved in water 148 prior to time $T_6$ is removed and that head space 152 is also free of ozone.

At time $T_7$, controller 128 will de-energize oxygen pump 116. Controller 128 will then open water outlet valve 106 and energize water pump 108 if clean water receptacle 112 has been positioned to receive water 148. Water 148, which is now relatively free of impurities subject to removal by ozonation, is pumped from contact chamber 102, through carbon filter 110 (which may remove other impurities from water 148) and dispensing nozzle 162 into clean water receptacle 112. One skilled in the art will be capable of configuring a detection device such as a microswitch to detect the presence of water receptacle 112. If clean water receptacle 112 is not correctly positioned at time $T_7$, water 148 remains in contact chamber 102.

At this point, the water purification cycle is complete. Controller 128 will then energize "Clean" indicator 144 and the user of water purification system 100 may use the clean water from clean water receptacle 112, if it was properly positioned at time $T_7$.

If water receptacle 112 was not properly positioned at time $T_7$, the clean water 148 may be dispensed through dispensing nozzle 162 by positioning a clean water receptacle 112 under dispensing nozzle 162 and then pressing "Dispense Water" button 164. Water will only be dispensed by "Dispense Water" button 164 is held pressed.

If time $T_5$ does not occur for a selected period of time $T_{max}$ (not shown) after the water purification cycle is initiated at time $T_1$ (i.e. $V_{sensor}$ does not flatten out as shown in FIG. 3), then controller 128 will terminate the water purification cycle and energize "Unable to Clean" indicator 146. The user may then attempt to clean water 148 again by pressing "Start Purification" pushbutton 142 or may discard and replace water 148 prior to commencing a new water purification cycle.

In some processes, such as the water purification process disclosed above, ozone is used for a specific purpose and then must be destroyed as is done using ozone destroyer 126. As described above, CARULITE 200 is an ozone destroying substance. If CARULITE 200 or another ozone destroying substance with the same electrical properties as CARULITE 200 is used as the sensing element 18 of ozone sensor 10, it may be possible to combine ozone sensor 20 and ozone destroyer 126 in water purification system 100 by positioning electrodes 20 and 22 on opposite longitudinal ends of the ozone destroyer.

Voltage and time values during a typical water purification cycle may have the following values:

| Name | Typical Value |
| --- | --- |
| $V_o$ | −50 mV to 50 mV |
| $V_\Delta$ | 10 mV |
| $V_c$ | $V_o$ + (70 to 100 mV) |
| A | 0 to 10 seconds |
| B | 60 seconds |
| C | 10 seconds |

Although the present invention has been described with reference to removing impurities from water by ozonating the water, the invention is equally applicable to any purification process where a different reactable gas is used to clean impurities from a liquid and the active component in the reactable gas is consumed as impurities are removed. In particular, the present invention may be used to monitor the progress of a water purification process using hydrogen peroxide ($H_2O_2$) as the reactable gas rather than ozone. It will be necessary to use a different sensing element 58 in this case, however, the structure and operation of the invention will remain the same in such an embodiment. Various other changes may be made to the invention without departing from its scope, which is limited only by the appended claims.

We claim:

1. A sensor for detecting ozone in an incoming gas stream, said sensor comprising:
   a. a sensing element comprising an ozone destroying material positioned in the flow path of the incoming gas stream, said sensing element being electrically sensitive to the presence of ozone such that an electrical potential is induced across said ozone destroying material; and
   b. an electrical circuit coupled to said sensing element for allowing said electrical potential to be measured.

2. The sensor of claim 1, said sensor further comprising a readout coupled to said electrical circuit, said readout being calibrated to indicate the concentration of ozone within the incoming gas stream.

3. The sensor of claim 1, wherein said sensor further comprises a housing having a gas inlet for receiving said incoming gas stream and a gas outlet for expelling an outgoing gas stream, and wherein said sensing element is positioned within said housing.

4. The sensor of claim 1 wherein said electrical potential correlates to the concentration of ozone in said gas stream.

5. The sensor of claim 4 wherein said electrical circuit comprises a first electrode and a second electrode, said electrodes being coupled across said sensing element at spaced points along the flow path of said off-gas stream and wherein said electrical potential may be measured across said first and second electrodes.

6. The sensor of claim 5 wherein said electrical circuit further comprises:
   a. a resistor coupled between said first and second electrodes for discharging said electric potential; and
   b. a capacitor coupled between said first and second electrodes for smoothing said electrical potential.

7. The sensor of claim 6 wherein said resistor has a resistance of at least 1 MΩ.

8. The sensor of claim 6 wherein said resistor has a resistance of at least 5 MΩ.

9. The sensor of claim 1 wherein said ozone destroying material is an ozone destroying catalyst for catalyzing the conversion of ozone into oxygen.

10. The sensor of claim 9 wherein said catalyst is selected from the group consisting of magnesium dioxide, copper oxide and combinations thereof.

11. An apparatus for removing impurities from water, said apparatus comprising:
   a. a contact chamber for containing said water, said contact chamber having an off-gas outlet for allowing off-gas to exit said contact chamber in an off-gas stream;
   b. a reactable gas source for providing a reactable gas;
   c. a reactable gas sensor including a sensing element across which an electrical potential is created due to exposure of the sensing element to the reactable gas, the sensor providing a reactable gas signal corresponding to the presence of reactable gas in said off-gas stream, said reactable gas sensor having an off-gas inlet and said off-gas inlet being in fluid communication with said off-gas outlet; and d. a controller, said controller being coupled to said sensing element for receiving said reactable signal and to said reactable gas source for controlling introduction of said reactable gas into said contact chamber in response to said reactable gas signal.

12. The apparatus of claim 11, wherein said reactable gas signal corresponds to the concentration of reactable gas in said off-gas stream.

13. The apparatus of claim 11, wherein said reactable gas is ozone.

14. The apparatus of claim 13 wherein: said sensing element includes a catalyst for decomposing ozone.

15. The apparatus of claim 14 wherein said reactable gas sensor includes an electrical circuit coupled between said sensing element and a signal node for conducting said potential to said signal node as said reactable gas signal, and wherein said electrical circuit includes:

a. a first electrode and a second electrode, said electrodes being coupled across said sensing element and being coupled to said signal node;

b. a resistor coupled between said first and second electrodes for discharging said potential; and c. a capacitor for smoothing said reactable gas signal.

16. The apparatus of claim 15 wherein said apparatus further comprises an ozone destroyer, and wherein:

a. said reactable gas sensor has a waste gas outlet for allowing said off-gas to exit off-gas sensor in a waste gas stream; and b. said ozone destroyer has:
  i. a waste gas inlet coupled to said waste gas outlet for receiving said waste gas stream;
  ii. an ozone removing element for removing ozone from said waste gas stream to produce an exhaust gas stream; and
  iii. an exhaust gas outlet for releasing said exhaust gas stream into the ambient environment.

17. The apparatus of claim 14 wherein said catalyst for decomposing ozone is selected from the group consisting of magnesium dioxide, copper oxide, and combinations thereof.

18. A method of removing impurities from an impure liquid, said method comprising the steps of:

a. providing a quantity of said impure liquid in a contact chamber;

b. providing a controller for controlling the flow of a treatment gas containing a reactable gas into said chamber;

c. initiating the flow of said treatment gas into said contact chamber, wherein said reactable gas flows through said liquid and wherein at least some of said reactable gas reacts with impurities in said liquid consuming at least some of said reactable gas, the remainder of said treatment gas collecting in said chamber as an off-gas;

d. withdrawing some of said off-gas;

e. monitoring the concentration of said reactable gas in said off-gas; and f. terminating the flow of said treatment gas in response to the rate of change of said concentration of said reactable gas in said off-gas falling below a selected level.

19. The method of claim 18 wherein step (e) comprises the steps of:

e.1. exposing a portion of said off-gas to a sensing element; and e.2. measuring an electrical potential across said sensing element, 20. The method of claim 19 wherein step (f) comprises the steps of:

f.1. tracking the electrical potential; and f.2. terminating the flow of said treatment gas in response to rate of change of the electrical potential falling below a selected level.

21. The method of claim 20 wherein:

i. said liquid is water containing impurities;

ii. said reactable gas is ozone; and iii. said detector includes a catalyst for converting ozone into oxygen, said catalyst being selected from the group consisting of magnesium dioxide, copper oxide, and combinations thereof.

22. A method of removing impurities from an impure liquid, said method comprising the steps of:

a. providing a quantity of said impure liquid in a contact chamber;

b. providing a supply of a reactable gas;

c. providing a controller for controlling the flow of said reactable gas into said contact chamber;

d. providing a sensor for measuring the concentration of said reactable gas in an off-gas stream exiting said chamber and providing an electrical signal corresponding to said concentration;

e. initiating the flow of said reactable gas into said chamber wherein said reactable gas flows through said liquid, and wherein at least some of said reactable gas reacts with impurities in said liquid consuming at least some of said reactable gas, the remainder of said reactable gas exiting said chamber in said off-gas stream;

f. monitoring said signal until the rate of change of said signal falls to a selected level;

g. terminating the flow of said reactable gas.

23. The method of claim 22 wherein step (b) is performed by taking the following steps:

b.1. providing an initial gas;

b.2. providing a reactable gas generator for converting a portion of said initial gas into said reactable gas, and wherein there is also provided an initial gas controller for controlling the flow of said initial gas into said chamber, and wherein the following steps are taken after step (g)

h. initiating the flow of said initial gas into said chamber;

i. waiting for a selected ozone clearing period; and j. terminating the flow of said initial gas.

24. The method of claim 23 wherein the following step is taken between steps (f) and (g):

f.1. waiting for a selected ozonation period.

25. The method of claim 22 wherein the following step is performed between steps (d) and (e):

d.1. recording an initial value of said signal, and wherein the following step is performed between steps (e) and (f):

e.1. monitoring said signal until the magnitude of said signal has changed from said initial value by a selected amount.

26. A method of removing impurities from an impure liquid said method comprising the steps of:

a. providing a quantity of said impure liquid in a reactor;

b. initiating the flow of ozone into said reactor, wherein said ozone flows through said liquid and wherein at least some of said ozone reacts with impurities in said liquid consuming at least some of said ozone, the remainder of said ozone producing an off-gas;

c. withdrawing at least some of said off-gas;

d. sensing the presence of said ozone in said off-gas using a sensing element comprising an ozone destroying material; and e. terminating the flow of said ozone in response to detection of a selected signal from said sensing element.

27. The method of claim 26, wherein the presence of said ozone is sensed based on the electrical potential across the sensing element and the selected signal is based on a particular electrical potential occurring across the sensing element.

28. The method of claim 27, wherein the selected signal corresponds to the concentration of said ozone in said off-gas.

29. The method of claim 27, wherein the selected signal corresponds to the rate of change of concentration of said ozone in said off gas.

30. The method of claim 26, wherein the selected signal corresponds to the concentration of said ozone in said off-gas.

31. The method of claim 26, wherein the selected signal corresponds to the rate of change of concentration of said ozone in said off gas.

* * * * *